(12) United States Patent
Mills

(10) Patent No.: US 8,241,263 B2
(45) Date of Patent: Aug. 14, 2012

(54) ABSORBENT ARTICLE

(75) Inventor: Andrew J. Mills, Mundelein, IL (US)

(73) Assignee: Medline Industries, Inc., Mundelein, IL (US)

( * ) Notice: Subject to any disclaimer, the term of this patent is extended or adjusted under 35 U.S.C. 154(b) by 1690 days.

(21) Appl. No.: 11/341,015

(22) Filed: Jan. 27, 2006

(65) Prior Publication Data

US 2007/0049896 A1  Mar. 1, 2007

Related U.S. Application Data

(60) Provisional application No. 60/712,023, filed on Aug. 26, 2005.

(51) Int. Cl.
*A61F 13/15* (2006.01)
*A61F 13/20* (2006.01)

(52) U.S. Cl. ............... 604/385.01; 604/389; 604/385.31

(58) Field of Classification Search ............. 604/385.01, 604/385.31, 386, 389–392
See application file for complete search history.

(56) References Cited

U.S. PATENT DOCUMENTS

| | | | |
|---|---|---|---|
| RE26,151 E | | 1/1967 | Duncan et al. |
| 4,317,449 A | | 3/1982 | Nowakoski |
| 4,662,875 A | * | 5/1987 | Hirotsu et al. ............... 604/389 |
| 4,846,815 A | * | 7/1989 | Scripps ......................... 604/391 |
| 4,963,140 A | * | 10/1990 | Robertson et al. ............ 604/389 |
| 5,026,446 A | | 6/1991 | Johnston et al. |
| 5,595,567 A | * | 1/1997 | King et al. .................... 604/391 |
| 5,897,546 A | * | 4/1999 | Kido et al. .................... 604/391 |
| 6,045,543 A | * | 4/2000 | Pozniak et al. ........... 604/385.01 |
| 6,448,202 B1 | | 9/2002 | Miyazawa et al. |
| 2004/0153046 A1 | * | 8/2004 | Ito et al. ....................... 604/391 |

FOREIGN PATENT DOCUMENTS

| | | | |
|---|---|---|---|
| EP | 0570980 B1 | * | 7/1997 |
| GB | 2135568 A | * | 9/1984 |
| JP | 2000-60899 A | * | 8/1998 |
| WO | WO 01/21126 A1 | * | 3/2001 |

OTHER PUBLICATIONS

Translation of JP 2000-60899.*
First Quality brochure entitled "Prevail Frontal Tape Adult Briefs Designed for Heavy Loss of Bladder and Bowel Control," Great Neck, NY, 1 page.
First Quality brochure entitled "Per-Fit Adult Briefs Designed for Moderate to Heavy Loss of Bladder and Bowel Control," Great Neck, NY, 1 page.
Kendall brochure entitled "Wings HL Ultra Hook & Loop Adult Brief," Mansfield, MA, 2 pages.
Kendall catalog internet sheet entitled "WINGS HL 3D Briefs," 1 page.

* cited by examiner

*Primary Examiner* — Tatyana Zalukaeva
*Assistant Examiner* — Susan Su
(74) *Attorney, Agent, or Firm* — Nixon Peabody LLP

(57) ABSTRACT

An absorbent article is disclosed. The article includes a first portion having at least two target strips located on opposite ends of the first portion, at least one visual sizing indicator positioned on the first portion of the article between the at least two target strips, a middle portion contoured inwards such that an hourglass shape is formed, and a second portion having at least two fasteners located on opposite edges of the second portion. The absorbent article is formed of several layers including a moisture-impervious outer layer, an inner layer substantially co-extensive with the outer layer, and a filler interposed between the inner layer and the outer layer.

19 Claims, 4 Drawing Sheets

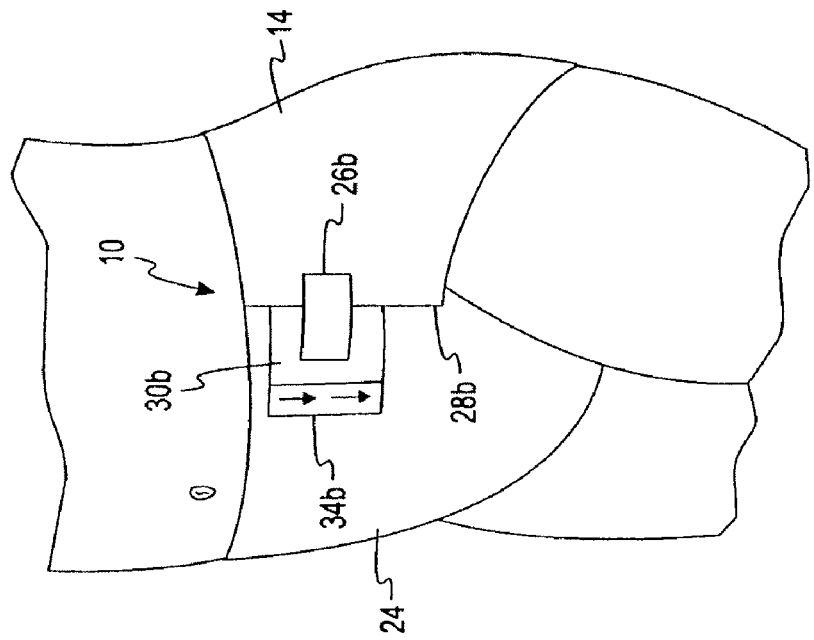
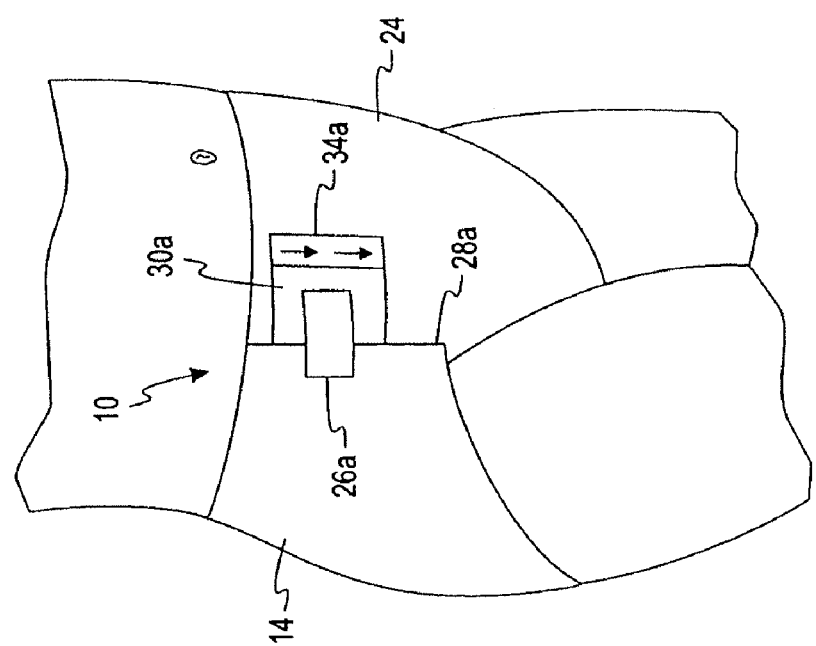

ABSORBENT ARTICLE

CROSS-REFERENCE TO RELATED APPLICATION

This application claims the benefit of U.S. Provisional Application No. 60/712,023, filed Aug. 26, 2005, which is hereby incorporated by reference in its entirety.

FIELD OF THE INVENTION

The present invention relates to an absorbent article and, more specifically, to using target strips and visual sizing indicators on the absorbent article to advise when to downsize an adult incontinent brief or disposable diaper to achieve a proper fit.

BACKGROUND OF THE INVENTION

Adult incontinent briefs, disposable diapers, and other absorbent articles are designed to absorb and contain liquid and other discharges from the human body to prevent body and clothing soiling. These absorbent articles typically have an outer layer of thin plastic film such as polyethylene, which may be reinforced at the areas where adhesive closure tabs are adhered during fastening of the absorbent article around a wearer. The reinforcement frequently may be a stronger plastic film that is adhesively attached to the outer layer and may be known as a target strip.

Often, an ill-fitting absorbent article is chosen for a wearer. One reason for the ill-fit is due to the fact that the size determination of absorbent articles is often based on a single criteria such as a wearer's weight, hip circumference, or waist circumference. Thus, other relevant factors such as age, height, thigh circumference, and rise are not taken into account. Alternatively, a wearer or caregiver may purposely choose a larger sized absorbent article under the mistaken belief that it will have a greater absorbency and hence be more beneficial. In reality, however, an oversized absorbent article may slip, slide, sag, or droop, any of which may cause discomfort and/or leakage.

Unlike determining that an absorbent article is too small for a wearer, determining that an absorbent article is too large for a wearer can be difficult and problematic. It is evident when an absorbent article is too small for a wearer because adhesive closure tabs, typically located on a back portion of the absorbent article, will not reach the target strips located on the front portion of the absorbent article, thus making it impossible to secure the absorbent article to the wearer. In contrast, when an absorbent article is too large for a wearer, the back portion may be wrapped around the wearer's waist, and the adhesive closure tabs may be adhered anywhere on the absorbent article, including portions located outside of the target strips. Because wearers of absorbent articles are often very young children or elderly persons, the wearers may be unable to walk or move freely and therefore may be unlikely to notice the absorbent article sagging or drooping. Moreover, the wearer may not be able to effectively communicate to his or her caregiver that the absorbent article is too large. In other cases, the ill-fit may be relatively subtle, leading the wearer to mistakenly believe that a proper fitting brief was chosen.

Downsizing an absorbent article has several benefits to the wearer. First, downsizing to an absorbent article that provides a better fit is likely to reduce leakage, since the smaller absorbent article will be less likely to slip, slide, sag, or droop. Moreover, downsizing an absorbent article may be more cost effective. Larger-sized absorbent articles are typically more expensive than smaller-sized absorbent articles of comparable absorbency. This is due to the fact that larger absorbent articles require the use of more absorbent materials and are thus more costly to manufacture. Often, a case of larger-sized absorbent articles will cost the same as smaller-sized absorbent articles but will contain considerably fewer absorbent articles.

Therefore, there exists a need to indicate to a wearer or caregiver when an absorbent article should be downsized.

SUMMARY OF THE INVENTION

According to one embodiment, an absorbent article comprises a first portion having at least two target strips located on opposite edges of the first portion, at least one visual sizing indicator positioned on the first portion of the article between the at least two target strips, a middle portion contoured inwards such that an hourglass shape is formed, and a second portion having at least two fasteners located on opposite edges of the second portion. The absorbent article is formed of several layers including a moisture-impervious outer layer, an inner layer substantially co-extensive with the outer layer, and a filler interposed between the inner layer and the outer layer.

According to another embodiment of the present invention, a method of determining that an absorbent article is too large for a wearer comprises the act of positioning the absorbent article on the wearer, the absorbent article comprising a first portion including at least two target strips positioned on opposite edges of the first portion and at least one visual sizing indicator located between the at least two target strips, and a second portion including at least two fasteners positioned on opposite edges of the second portion. The method further comprises the act of pulling the opposite edges of the second portion in opposite directions such that the second portion is stretched to form a snug fit to the wearer. The method further comprises attaching the at least two fasteners to the first portion. The method further comprises determining whether the absorbent article should be downsized based on whether the at least two fasteners overlap the at least one visual sizing indicator when attached to the first portion.

According to another embodiment of the present invention, an absorbent article comprises a first portion having at least two target strips located on opposite edges of the first portion, at least one visual sizing indicator positioned on the first portion of the article between the at least two target strips, a middle portion contoured inwards such that an hourglass shape is formed, and a second portion having at least two fasteners located on opposite edges of the second portion.

The above summary of the present invention is not intended to represent each embodiment or every aspect of the present invention. The detailed description and Figures will describe many of the embodiments and aspects of the present invention.

BRIEF DESCRIPTION OF THE DRAWINGS

The foregoing and other advantages of the invention will become apparent upon reading the following detailed description and upon reference to the drawings.

FIG. 2 illustrates a cross-section generally taken through section line 2-2 of the brief of FIG. 1a.

FIG. 3a illustrates a right side view of the brief of FIG. 1a, the brief being secured and fit-appropriate to a wearer.

FIG. 3b illustrates a left side view of the brief of FIG. 3a.

FIG. 4b illustrates a left side view of the brief of FIG. 4a.

Figure 1A:
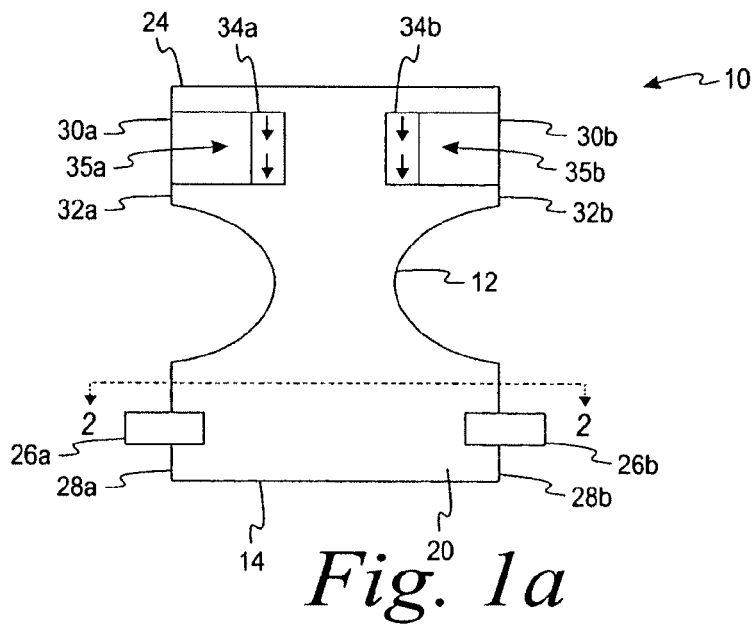
FIG. 1a illustrates a top view of an outer layer of an open adult incontinent brief, according to one embodiment of the present invention.

While the invention is susceptible to various modifications and alternative forms, specific embodiments have been shown by way of example in the drawings and will be described in detail herein. It should be understood, however, that the invention is not intended to be limited to the particular forms disclosed. Rather, the invention is to cover all modifications, equivalents, and alternatives falling within the spirit and scope of the invention.

DESCRIPTION OF ILLUSTRATIVE EMBODIMENTS

The present invention is directed to an absorbent article having target strips and indicators to advise a wearer or caregiver when the absorbent article is too large for the wearer. Although the remainder of the disclosure herein will be directed toward an adult incontinent brief, it is to be understood that the invention may also be implemented on other absorbent articles, including disposable diapers.

Figure 2:
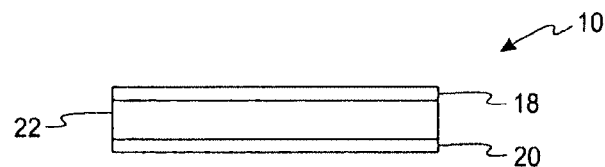

Turning first to FIG. 1a, the outer layer 20 of an adult incontinent brief 10 according to one embodiment of the present invention is illustrated. The brief 10 is of substantially rectangular configuration. In this embodiment, the middle portion 12 is contoured in an "hourglass" configuration to fit around a wearer's thighs when the brief 10 is secured to the wearer. The brief 10 also includes a front portion 24 and a back portion 14. The brief 10 generally consists of several layers, as shown in FIG. 2. FIG. 2 is a cross-sectional view of the brief 10 generally along section line 2-2 shown in FIG. 1a. The brief 10 includes an inner layer 18, which faces a wearer when the brief 10 is secured to the wearer. The inner layer 18 may be comprised of a nonwoven topsheet. The brief 10 also includes a moisture-impervious outer layer 20, which faces away from a wearer when the brief 10 is secured to the wearer. This outer layer 20 is substantially co-extensive with the inner layer 18. The outer layer 20 may be made of any material suitable to minimize fluids and other discharge from escaping the brief, including polyethylene and/or breathable poly. A filler layer 22 is positioned between the inner layer 18 and the outer layer 20. The absorbency of the brief generally may range from about 250 cc to about 2,000 cc. The filler layer 22 may be composed of any materials suitable for absorbing fluids and discharge, including super absorbent polymer (SAP) and fluff.

Referring back to FIG. 1a, a top view of the outer layer 20 of the brief 10 is shown. The brief 10 includes features designed for securing the brief 10 to a wearer. For example, the brief 10 has fasteners 26a, 26b positioned on opposite side edges 28a, 28b of the brief 10. In the embodiment of FIG. 1a, the fasteners 26a, 26b are positioned on the back portion 14 of the brief 10. The fasteners 26a, 26b extend over the side edges 28a, 28b of the back portion 14, thus allowing the fasteners 26a, 26b to contact and attach to the front portion 24 when the brief 10 is folded and positioned on a wearer, as shown in FIGS. 3a and 3b. The types of fasteners 26a, 26b may include pressure sensitive adhesive tape or other adhesive materials, tab members having adhesive on one side, Velcro®, safety pins, hook and loop type latches, and/or other means suitable for attaching the back portion 14 to the front portion 24 such that the brief 10 may be secured to a wearer. Adult incontinent briefs may include at least two fasteners per side to ensure both a tight fit around the wearer's waist as well as a tight or sealed gasket in the wearer's crotch area to prevent leakage.

The brief 10 of the present invention also includes target strips 30a, 30b. The target strips 30a, 30b are areas where the fasteners 26a, 26b are to be attached to the front portion 24 during securing of the brief 10 around a wearer. The target strips 30a, 30b may include a frontal tape landing zone(s) or adhesive label imprinted material(s). A frontal tape landing zone may include a section of tape positioned on the front portion 24 of the brief 10 to which the fastener(s) 26a, 26b may be fastened. The frontal tape landing zone may include an adhesive label imprinted material. The adhesive label imprinted material may be imprinted with text, characters, graphics, fabrics, other indicia, or a combination thereof. The target strips 30a, 30b may comprise an area of reinforced material, such as a stronger plastic film or biaxially oriented polypropylene (BOPP). The area of reinforced material is frequently comprised of a stronger plastic film that is adhesively attached to the outer layer 20. The area of reinforced material may be particularly useful in embodiments where the type of fastener(s) 26a, 26b includes an adhesive tape or the like so that the fastener(s) 26a, 26b may be removed from the area of reinforced material without damaging the brief 10. The target strips 30a, 30b may include other distinct physical characteristics to enhance the ability to secure the fasteners 26a, 26b to the brief 10, thereby decreasing the likelihood of the fasteners 26a, 26b becoming unfastened. The target strips 30a, 30b may, for example, generally have a width of approximately 165 mm and a length of approximately 165 mm for size large, extra-large (XL), and double extra-large (XXL) briefs. Size small, medium, and regular briefs may, for example, generally have a width of approximately 165 mm and a length of approximately 140 mm. It is contemplated that the target strips 30a, 30b may also have other lengths and widths. The target strips 30a, 30b shown in this embodiment are generally rectangular in shape. It is contemplated that they may take the form of other shapes, including, but not limited to, squares, polygons, or circles.

The target strips 30a, 30b are located on the portion of the brief 10 generally opposite the fasteners 26a, 26b. In the embodiment of FIG. 1a, the target strips 30a, 30b are located at or near the side edges 32a, 32b of the front portion 24. It is contemplated that the fasteners 26a, 26b may be positioned on the front portion 24 of the brief 10, and the target strips 30a, 30b may be positioned on the back portion 14 of the brief 10. However, it may be more convenient to place the fasteners 26a, 26b on the back portion 14 of the brief 10 so that the fasteners 26a, 26b may be secured to the front portion 24, thus making it unnecessary to reach behind the wearer, who is often lying down, in order to secure the fasteners 26a, 26b. In some embodiments, the target strips 30a, 30b are visually distinct from other areas of the brief 10 so that the wearer or caregiver may readily recognize the areas where the fasteners 26a, 26b should optimally attach to the brief 10. For example, the target strips 30a, 30b may include text, characters, graphics, fabrics, or a combination thereof, including happy faces, green lights, or other indicia, different from the rest of the brief 10 and suitable for indicating that a proper fit has been achieved.

Figure 1B:
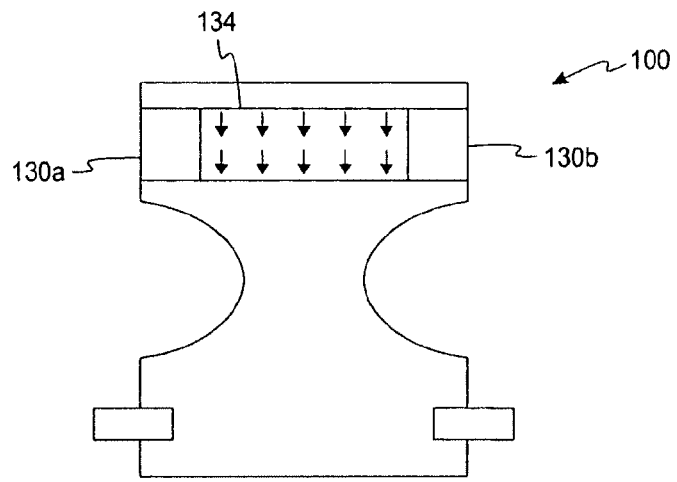
FIG. 1b illustrates a top view of an outer layer of an open adult incontinent brief, according to another embodiment of the present invention.

The brief 10 also includes visual sizing indicators 34a, 34b. As shown in FIG. 1a, the visual sizing indicators 34a, 34b may be located adjacent to the target strips 30a, 30b on the inner sides 35a, 35b of the target strips 30a, 30b opposite the side edges 32a, 32b of the brief 10. In another embodiment, the visual sizing indicators 34a, 34b may be located on the target strips 30a, 30b in an area adjacent to the inner sides 35a, 35b. As demonstrated in the embodiment of FIG. 1b, it is further contemplated that a single visual sizing indicator 134 may be positioned adjacent to and between the target strips 130a, 130b, thereby connecting the first target strip 130a to the second target strip 130b of the brief 100.

Referring back to FIG. 1a, the purpose of the visual sizing indicators 34a, 34b is to indicate to a wearer or a caregiver securing the brief 10 to the wearer that the brief 10 is too large and should be downsized. FIGS. 3a and 3b show the brief 10 of FIG. 1a being fit-appropriate and positioned on a wearer. In order to secure the brief 10 to the wearer, the side edges 28a, 28b of the back portion 14 are grasped and pulled in opposite directions, laterally and outwardly, stretching the back portion 14 so that it lies flat and snug against the wearer. Each of the side edges 28a, 28b should be pulled with generally the same amount of force so that the brief 10 remains positioned generally evenly and symmetrically on the wearer. The side edges 32a, 32b of the front portion 24 are also pulled so that the front portion 24 lies flat and snug against the wearer's abdomen. The brief 10 is then secured to the wearer by securing the fasteners 26a, 26b to a section of the front portion 24 of the brief 10 located as far around the wearer's waist as the fasteners 26a, 26b will comfortably reach so that the side edges 28a, 28b of the back portion 14 overlap the side edges 32a, 32b of the front portion 24.

If, when the brief 10 is secured to a wearer, the fasteners 26a, 26b attach to the front portion 24 of the brief 10 in an area overlapping the target strips 30a, 30b, as shown in FIGS. 3a and 3b, the correct size brief has been chosen. FIG. 3a shows the right side of the brief 10 fastened to a wearer where the brief 10 is secured and fit-appropriate to the wearer. FIG. 3b shows the left side of the brief 10 of FIG. 3a. The proper fit of the brief 10 may be illustrated to the wearer or caregiver through the target strips 30a, 30b distinguishable by the text, characters, graphics, fabrics, other indicia, or combinations thereof of the target strips 30a, 30b.

Figure 4A:
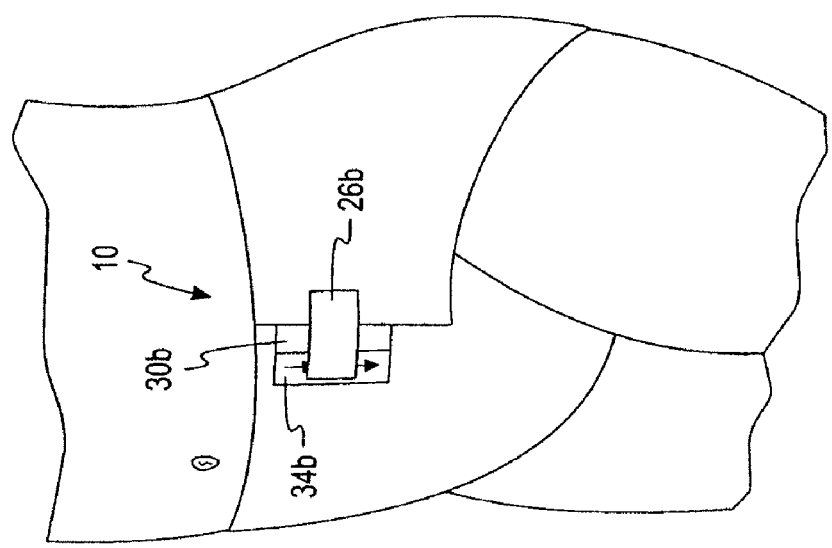
FIG. 4a illustrates a right side view of the brief of FIG. 1a, the brief being secured and ill-fitted to a wearer.
Figure 4B:
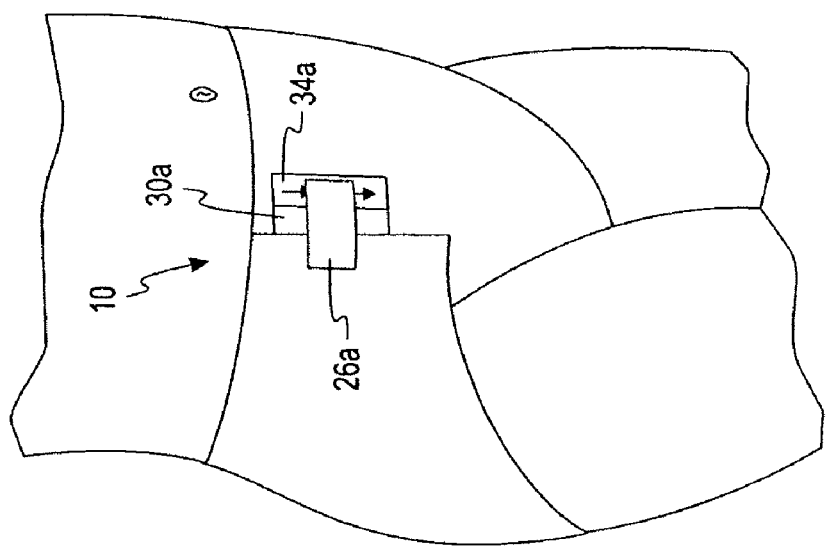
Figure 5:
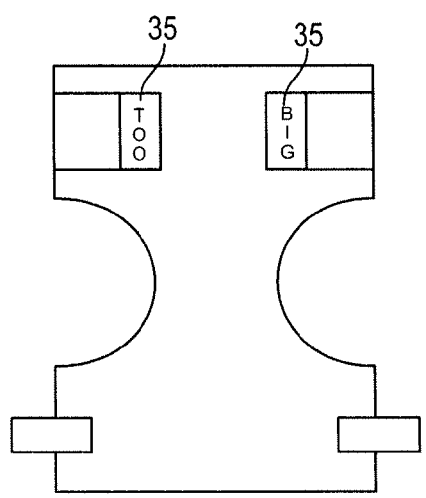
FIGS. 5-7 illustrate top views of outer layers of open adult incontinent briefs, according to other embodiments of the present invention.
Figure 6:
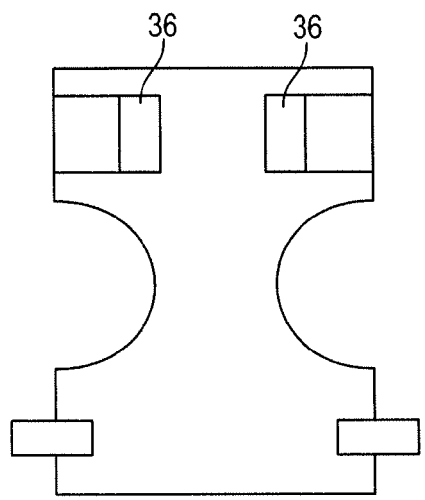
Figure 7:
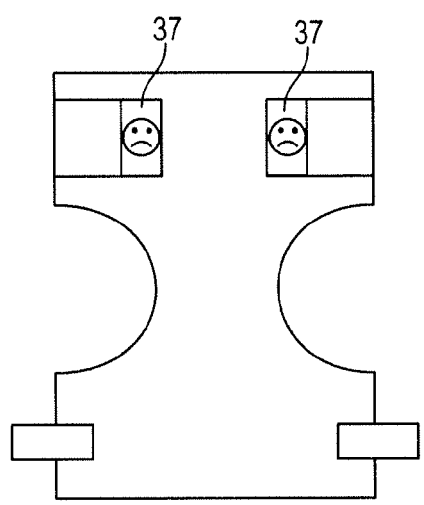

If, when the brief 10 is secured to a wearer, the fasteners 26a, 26b attach to the front portion 24 of the brief 10 in the area overlapping the visual sizing indicators 34a, 34b, as shown in FIGS. 4a and 4b, the brief 10 is too large for the wearer. FIG. 4a shows the right side of a brief 10 fastened to a wearer where the brief is secured but ill-fitted to the wearer. FIG. 4b shows the left side of the brief 10 of FIG. 4a. The visual indicators 34a, 34b may include indicia such as, but not limited to, text (see text 35 of FIG. 5), characters, graphics, fabrics (see fabric 36 of FIG. 6), other indicia, or combinations thereof, to indicate to the wearer or caregiver that the brief 10 is too large and should be downsized. In the embodiment shown, arrows pointing downward are used to suggest downsizing the brief 10. Other indicia may include, but is not limited to sad faces graphics (see sad faces graphic 37 of FIG. 7), red lights or color, or other characters suitable for indicating that an ill-fit has been achieved. The visual sizing indicators 34a, 34b should be distinguishable from the target strips 30a, 30b, thus making it evident to the wearer or caregiver that the brief 10 is too large for the wearer because the fasteners 26a, 26b are being secured to the brief 10 in an area outside the target strip 30a, 30b and within the area of the visual sizing indicators 34a, 34b.

According to alternative embodiment A, an absorbent article comprises a first portion having at least two target strips located on opposite ends of the first portion, at least one visual sizing indicator positioned on the first portion of the article between the at least two target strips, a middle portion contoured inwards such that an hourglass shape is formed, and a second portion having at least two fasteners located on opposite edges of the second portion, wherein the absorbent article is formed of several different layers, including a moisture-impervious outer layer, an inner layer substantially co-extensive with the outer layer, and a filler interposed between the inner layer and the outer layer.

According to alternative embodiment B, the absorbent article of alternative embodiment A, wherein the absorbent article is an adult incontinent brief.

According to alternative embodiment C, the article of alternative embodiment A, wherein the absorbent article is a disposable diaper.

According to alternative embodiment D, the absorbent article of alternative embodiment A, wherein the at least two fasteners are tab members having adhesive on one side.

According to alternative embodiment E, the absorbent article of alternative embodiment A, wherein the first portion is a front portion and the second portion is a back portion when the absorbent article is positioned on a wearer.

According to alternative embodiment F, the absorbent article of alternative embodiment A, wherein the at least two target strips are comprised of a reinforced material.

According to alternative embodiment G, the absorbent article of alternative embodiment A, wherein the at least two target strips include text, characters, graphics, fabrics, or a combination thereof.

According to alternative embodiment H, the absorbent article of alternative embodiment A, wherein the at least one visual sizing indicator includes arrows, text, characters, graphics, fabrics, or a combination thereof.

According to alternative embodiment I, a method of determining that an absorbent article is too large for a wearer comprises the acts of positioning the absorbent article on the wearer, the absorbent article comprising a first portion including at least two target strips positioned on opposite edges of the first portion and at least one visual sizing indicator located between the at least two target strips, and a second portion including at least two fasteners positioned on opposite edges of the second portion, pulling the opposite edges of the second portion in opposite directions such that the second portion is stretched to form a snug fit to the wearer, attaching the at least two fasteners to the first portion, and determining whether the absorbent article should be downsized based on whether the fasteners overlap the at least one visual sizing indicator when attached to the first portion.

According to alternative embodiment J, the method of alternative embodiment I, wherein the at least two fasteners overlapping the at least two target strips indicate that the absorbent article is an appropriate fit for the wearer.

According to alternative embodiment K, the method of alternative embodiment I, wherein the at least two fasteners overlapping the at least one visual sizing indicator indicate that the absorbent article should be downsized for the wearer.

According to alternative embodiment L, the method of alternative embodiment I, wherein the absorbent article is an adult incontinent brief.

According to alternative embodiment M, the method of alternative embodiment I, wherein the absorbent article is a disposable diaper.

According to alternative embodiment N, the method of alternative embodiment I, wherein the at least two fasteners are tab members having adhesive on one side.

According to alternative embodiment O, the method of alternative embodiment I, wherein the first portion is a front portion and the second portion is a back portion when the absorbent article is positioned on the wearer.

According to alternative embodiment P, the method of alternative embodiment I, wherein the at least two target strips are comprised of a reinforced material.

According to alternative embodiment Q, the method of alternative embodiment I, wherein the at least two target strips include text, characters, graphics, fabrics, or a combination thereof.

According to alternative embodiment R, the method of alternative embodiment I, wherein the at least one visual sizing indicator includes arrows, text, characters, graphics, fabrics, or a combination thereof.

According to alternative embodiment S, an absorbent article comprises a first portion having at least two target strips located on opposite ends of the first portion, at least one visual sizing indicator positioned on the first portion of the article between the at least two target strips, a middle portion contoured inwards such that an hourglass shape is formed, and a second portion having at least two fasteners located on opposite edges of the second portion.

According to alternative embodiment T, an absorbent article of alternative embodiment S, wherein the at least one visual sizing indicator is two visual sizing indicators, the two visual sizing indicators being formed on the at least two target strips.

According to alternative embodiment U, the absorbent article of alternative embodiment S, wherein the at least one visual sizing indicator is two visual sizing indicators, the two visual sizing indicators being positioned adjacent to the at least two target strips.

According to alternative embodiment V, an absorbent article comprises a first portion having at least two target strips located on opposite ends of the first portion, at least one visual sizing indicator positioned on the first portion of the article between the at least two target strips, a middle portion contoured inwards such that an hourglass shape is formed, and a second portion having at least two fasteners located on opposite edges of the second portion, wherein the article is formed of several layers including a moisture-impervious outer layer, an inner layer substantially co-extensive with the outer layer, and a filler interposed between the inner layer and the outer layer.

According to alternative embodiment W, the article of alternative embodiment V, wherein the at least two target strips include at least one character, graphic, fabric, text or a combination thereof.

According to alternative embodiment X, the article of alternative embodiment V, wherein the at least one visual sizing indicator includes at least one arrow, text, character, graphic, fabric, or a combination thereof.

According to alternative embodiment Y, a method of determining that an absorbent article is too large for a wearer comprises the acts of positioning the article on the wearer, the article comprising a first portion including at least two target strips positioned on opposite edges of the first portion and at least one visual sizing indicator located between the at least two target strips, and a second portion including at least two fasteners positioned on opposite edges of the second portion, pulling the opposite edges of the second portion in opposite directions such that the second portion is stretched to form a snug fit to the wearer, attaching the at least two fasteners to the first portion, and determining whether the article should be downsized based on whether the at least two fasteners overlap the at least one visual sizing indicator when attached to the first portion.

According to alternative embodiment Z, the method of alternative embodiment Y, wherein the at least two target strips include at least one character, graphic, fabric, text, or a combination thereof.

According to alternative embodiment AA, the method of alternative embodiment Y, wherein the at least one visual sizing indicator includes at least one arrow, text, character, graphic, fabric, or a combination thereof.

While the present invention has been described with reference to one or more particular embodiments, those skilled in the art will recognize that many changes may be made thereto without departing from the spirit and scope of the present invention. Each of these embodiments and obvious variations thereof is contemplated as falling within the spirit and scope of the invention, which is set forth in the following claims.

What is claimed is:

1. An absorbent article comprising:
 a first portion having at least two target strips located on opposite edges of the first portion;
 at least one visual sizing indicator positioned on the first portion of the article between the at least two target strips;
 a middle portion contoured inwards such that an hourglass shape is formed; and
 a second portion having at least two fasteners located on opposite edges of the second portion,
 wherein the article is formed of several layers including a moisture-impervious outer layer, an inner layer substantially co-extensive with the outer layer, and a filler interposed between the inner layer and the outer layer.

2. The article of claim 1, wherein the article is an adult incontinent brief.

3. The article of claim 1, wherein the article is a disposable diaper.

4. The article of claim 1, wherein the at least two fasteners are tab members having adhesive on one side.

5. The article of claim 1, wherein the first portion is a front portion and the second portion is a back portion when the article is positioned on a wearer.

6. The article of claim 1, wherein the at least two target strips are comprised of a reinforced material.

7. The article of claim 1, wherein the at least two target strips include at least one character, graphic, fabric, text or a combination thereof.

8. The article of claim 1, wherein the at least one visual sizing indicator includes at least one arrow, text, character, graphic, fabric, or a combination thereof.

9. A method of determining that an absorbent article is too large for a wearer comprising:
 positioning the article on the wearer, the article comprising a first portion including at least two target strips positioned on opposite edges of the first portion and at least one visual sizing indicator located between the at least two target strips, and a second portion including at least two fasteners positioned on opposite edges of the second portion;
 pulling the opposite edges of the second portion in opposite directions such that the second portion is stretched to form a snug fit to the wearer;
 attaching the at least two fasteners to the first portion; and
 determining whether the article should be downsized based on whether the at least two fasteners overlap the at least one visual sizing indicator when attached to the first portion.

10. The method of claim 9, wherein the at least two fasteners overlapping the at least two target strips indicate that the article is an appropriate fit for the wearer.

11. The method of claim 9, wherein the article is an adult incontinent brief.

12. The method of claim 9, wherein the article is a disposable diaper.

13. The method of claim 9, wherein the at least two fasteners are tab members having adhesive on one side.

14. The method of claim 9, wherein the first portion is a front portion and the second portion is a back portion when the article is positioned on the wearer.

15. The method of claim 9, wherein the at least two target strips are comprised of a reinforced material.

16. The method of claim 9, wherein the at least two target strips include at least one character, graphic, fabric, text, or a combination thereof.

17. The method of claim 9, wherein the at least one visual sizing indicator includes at least one arrow, text, character, graphic, fabric, or a combination thereof.

18. An absorbent article comprising:
  a first portion having at least two target strips located on opposite edges of the first portion;
  at least one visual sizing indicator positioned on the first portion of the article between the at least two target strips;
  a middle portion contoured inwards such that an hourglass shape is formed; and
  a second portion having at least two fasteners located on opposite edges of the second portion.

19. The absorbent article of claim 18, wherein the at least one visual sizing indicator is two visual sizing indicators, the two visual sizing indicators being positioned adjacent to the at least two target strips.

* * * * *